US008764803B2

(12) United States Patent
Suddaby

(10) Patent No.: US 8,764,803 B2
(45) Date of Patent: Jul. 1, 2014

(54) APPARATUS AND METHOD FOR ALIGNING A SPINE

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 96 days.

(21) Appl. No.: 13/644,365

(22) Filed: Oct. 4, 2012

(65) Prior Publication Data

US 2014/0100612 A1 Apr. 10, 2014

(51) Int. Cl.
*A61B 17/70* (2006.01)
*A61B 17/88* (2006.01)
*A61B 17/68* (2006.01)

(52) U.S. Cl.
CPC ............ *A61B 17/7053* (2013.01); *A61B 17/88* (2013.01); *A61B 17/7056* (2013.01); *A61B 2017/681* (2013.01); *A61B 17/7071* (2013.01)
USPC ............................. 606/263; 606/279; 606/277

(58) Field of Classification Search
CPC ........... A61B 17/7053; A61B 17/7056; A61B 17/7058; A61B 17/7071
USPC ............................ 606/263, 273, 276, 277, 279
See application file for complete search history.

(56) References Cited

U.S. PATENT DOCUMENTS

| | | | |
|---|---|---|---|
| 4,047,523 A | 9/1977 | Hall | |
| 5,782,831 A * | 7/1998 | Sherman et al. | 606/86 A |
| 6,033,429 A | 3/2000 | Magovern | |
| 6,077,268 A | 6/2000 | Farris et al. | |
| 6,290,700 B1 | 9/2001 | Schmotzer | |
| 6,423,065 B2 | 7/2002 | Ferree | |
| 6,551,320 B2 | 4/2003 | Lieberman | |
| 6,648,890 B2 | 11/2003 | Culbert et al. | |
| 6,676,665 B2 | 1/2004 | Foley et al. | |
| 7,632,277 B2 | 12/2009 | Woll et al. | |
| 2006/0047282 A1 | 3/2006 | Gordon | |
| 2006/0195090 A1 | 8/2006 | Suddaby | |
| 2009/0088799 A1 | 4/2009 | Yeh | |
| 2009/0093820 A1 | 4/2009 | Trieu et al. | |
| 2009/0112262 A1 | 4/2009 | Pool et al. | |
| 2009/0112263 A1 | 4/2009 | Pool et al. | |
| 2010/0145392 A1 * | 6/2010 | Dutoit et al. | 606/279 |
| 2010/0185241 A1 * | 7/2010 | Malandain | 606/263 |

(Continued)

OTHER PUBLICATIONS

Cundy, Peter J.; Paterson, Dennis C.; Hillier, Terence M.; Sutherland, Andrew D.; Stephen, John P.; Foster, Bruce K., Cotrel-Dubousset Instrumentation and Vertebral Rotation in Adolescent Idiopathic Scoliosis. The Journal of Bone and Joint Surgery, 1990, pp. 670-674, J Bone Joint Surg, British Editorial Society of Bone and Joint Surgery.

*Primary Examiner* — Ellen C Hammond
(74) *Attorney, Agent, or Firm* — Simpson & Simpson, PLLC

(57) ABSTRACT

The present invention broadly comprises an assembly for performing a gradual lateral spinal alignment of a spine. The assembly includes a toggle bolt that includes a shaft and a toggle wing, a rigid stabilizing rod with an orifice, a cable attached to the toggle bolt and a tube enclosing the cable and extending out of the patient's back. The toggle bolt extends through the stabilizing rod and is positioned against the misaligned spine. The toggle bolt is placed in a bore through the body of a vertebra and deployed. The attached cable is pulled using the stabilizing rod as a brace to pull the spine into alignment. The device allows the spine to be gradually placed into alignment helping to avoid trauma on the spine and surrounding tissue.

18 Claims, 12 Drawing Sheets

(56) References Cited

U.S. PATENT DOCUMENTS

| | | | |
|---|---|---|---|
| 2010/0318129 A1* | 12/2010 | Seme et al. | 606/254 |
| 2011/0054536 A1* | 3/2011 | Elsebaie et al. | 606/264 |
| 2011/0066188 A1* | 3/2011 | Seme et al. | 606/264 |
| 2012/0059419 A1* | 3/2012 | Alamin et al. | 606/263 |
| 2012/0059423 A1* | 3/2012 | Young | 606/279 |
| 2012/0203282 A1* | 8/2012 | Sachs et al. | 606/278 |
| 2013/0211455 A1* | 8/2013 | Seme | 606/257 |

* cited by examiner

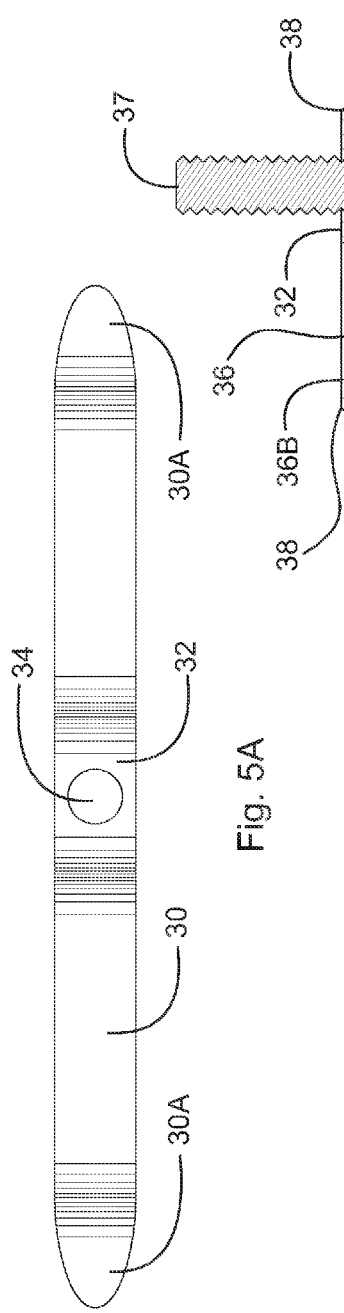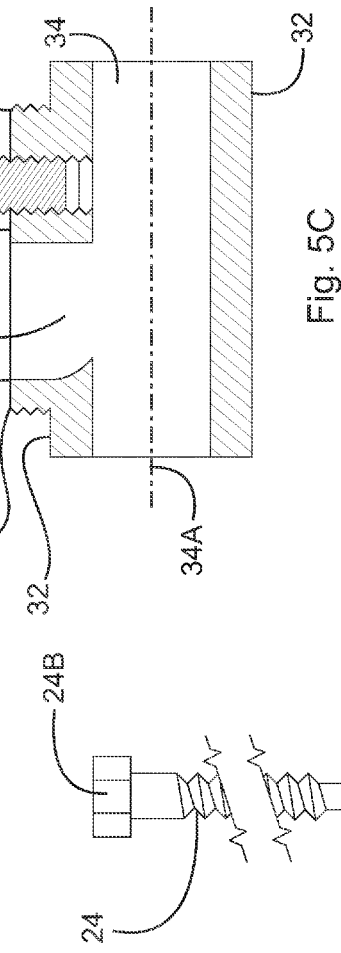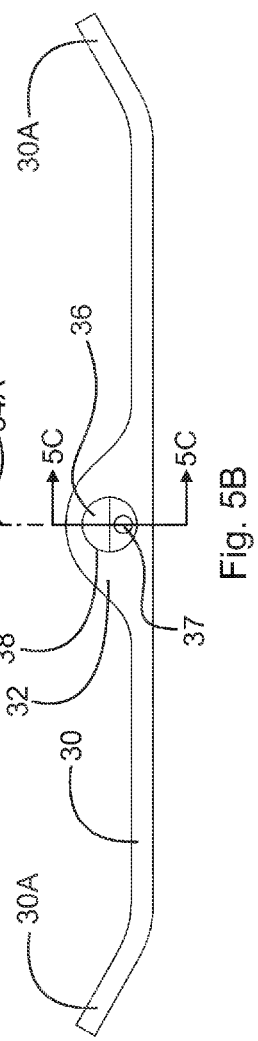

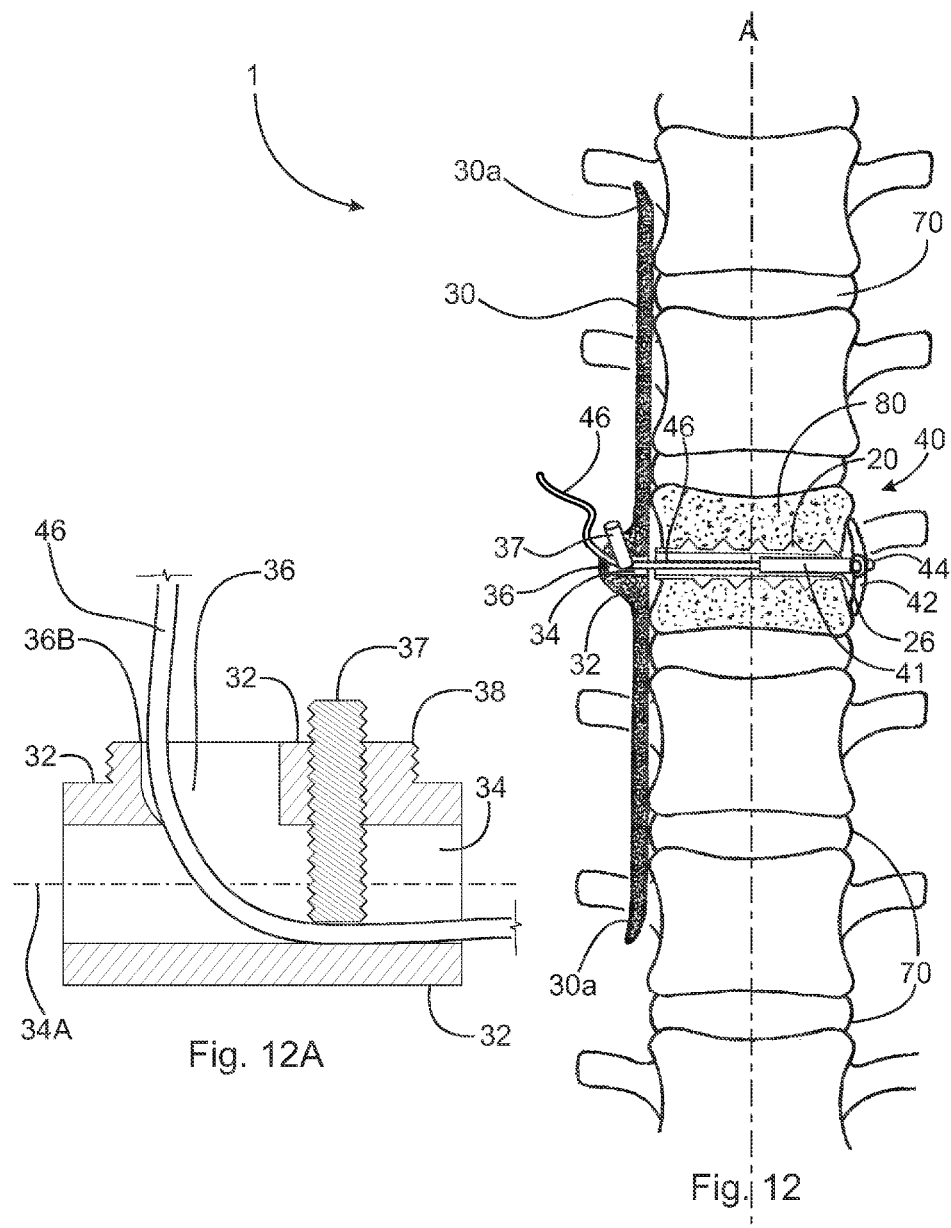

APPARATUS AND METHOD FOR ALIGNING A SPINE

FIELD OF THE INVENTION

The field of the invention pertains to the field of surgical devices, particularly to orthopedic surgical device, and more particularly to corrective devices related to the spine.

BACKGROUND OF THE INVENTION

Scoliosis is a disorder that causes an abnormal curve of the spine, or backbone. Patients with scoliosis develop abnormal curves to either side of the body's median line (lateral curve) and the bones of the spine twist on each other like a corkscrew. Scoliosis is about two times more common in girls than boys. It can be seen at any age, but it is most common in those over 10 years old.

Often, the cause of scoliosis is unknown and is described based on the age when scoliosis develops. If the person is less than 3 years old, it is called infantile idiopathic scoliosis. Scoliosis that develops between 3 and 10 years of age is called juvenile idiopathic scoliosis, and people that are over 10 years old have adolescent idiopathic scoliosis.

In functional scoliosis, the spine is normal, but an abnormal curve develops because of a problem somewhere else in the body. This could be caused by one leg being shorter than the other or by muscle spasms in the back. In the neuromuscular form, there is a problem during the formation of the bones of the spine. Either the bones of the spine fail to form completely or they fail to separate from each other. This type of scoliosis may develop in people with other disorders including birth defects, muscular dystrophy, cerebral palsy, and Marfan's disease. This type of scoliosis is often much more severe and needs more aggressive treatment than other forms of scoliosis. Degenerative scoliosis occurs in older adults. It is caused by changes in the spine due to arthritis. Weakening of the normal ligaments and other soft tissues of the spine combined with abnormal bone spurs can lead to an abnormal curvature of the spine.

Adolescent idiopathic scoliosis is the most common form of scoliosis. If the angle of the spinal curve (Cobb's angle) is small when first diagnosed, it can be observed and followed with routine X-rays and measurements. If the curve stays below 25 degrees, no other treatment is usually needed. If the curve is between 25-40 degrees, a brace may be recommended. If the curve is greater than 40 degrees, then surgery may be recommended. Braces are not designed to correct the curve. They are used to help slow or stop the curve from getting worse.

Spinal fusion is one surgical procedure that may be used to alleviate scoliosis. In this procedure, bone is grafted to the vertebrae to form a rigid column. The rigidity of the column will prevent the curve from worsening. However, the rigid column reduces the range of motion available to the patient.

Modern surgical procedures attempt to address sagittal imbalance and rotational defects unresolved by the earlier rod systems. They primarily involve a combination of rods, screws, hooks, cables and/or wires fixing the spine and applying forces to the spine to correct the spinal curvature. An example of the use of screws and cables is seen in U.S. Patent Application Publication No. 2006/0195090 to Suddaby ("Suddaby") which is hereby incorporated by reference in its entirety. Suddaby discloses a system for improving the alignment of a spine by placing a series of screws or pins into the posterior or lateral side of the bodies of individual vertebrae. Hollow spacers are placed between the pins and a cable is extended through the heads of the pins and the spacers and is attached to an expansion sleeve. Tension is applied to the cable by pulling it through the expansion sleeve and then applying tension to the cable to pull the attached pins into an improved alignment. One of a plurality of nodules at the end of the cable is then placed into the passage of the expansion sleeve thereby holding the cable in the new "tensioned" position. The tension discourages movement of the spine.

U.S. Pat. No. 6,551,320 to Lieberman ("Lieberman"), hereby incorporated by reference in its entirety, discloses an apparatus for aligning a spine that includes a plurality of anchors screwed into adjacent vertebral bodies. A cable or series of cables is strung through or around the anchors and then pulled. The tension applied to the cable(s) is used to pull the spine into a desired alignment. U.S. Patent Application Publication No. 2009/0112262 to Pool, et al. ("Pool"), hereby incorporated by reference in its entirety, discloses a system in which at least one anchor is screwed or otherwise embedded into an upper vertebra and one or more anchors are similarly placed in lower vertebra(ae). A cable is extended between the anchors and force applied to the cable by a magnetic adjustment device to align the spine. In some cases a second anchor-cable arrangement can be used on the opposite side of the spine.

Finally, U.S. Pat. No. 5,782,831 to Sherman, et al. ("Sherman"), hereby incorporated by reference in its entirety, discloses a system for reducing a displaced vertebra between adjacent vertebrae. The Sherman patent describes a system in which two anchors are screwed into the vertebrae on either side of the displaced vertebra with a rod attached between the anchors. A third anchor is screwed into the displaced vertebra and attached to a cable. A cable tightening device, such as a come-along type device is used to pull the displaced vertebra into alignment after which it is attached to the support rod. However, the attachment of a bar across three adjacent vertebrae prevents pulling a curved spine into a more proper alignment.

In attempting to solve spinal alignment and displacement problems, the prior art relies on multiple vertebral anchors and the application of alignment force through complicated force applicators and cable systems. Often such corrective systems fail to provide complete correction of spinal alignment as full recuperation requires either too much force to correct the curve or sudden, rapid stretching of spinal neural elements resulting in permanent neurological damage.

What is needed then is an apparatus for aligning the spine that possesses few parts and is easy to implant while enabling a gradual restoration of the of spinal alignment over a determined period of time so that large and/or sudden forces are not applied to the curved spine. By applying reduced corrective forces over a longer period of time, complications such as bone fracture and nerve damage can be reduced or avoided.

SUMMARY OF THE INVENTION

The present invention broadly comprises an assembly for performing a gradual lateral spinal alignment of a spine, the spine to be realigned having a lateral curve, the lateral curve having a convex side and an opposite concave side. The assembly comprises a hollow bone screw having internal threads and an open proximal end and an open distal end, a second screw threadably inserted into the hollow bone screw, a toggle bolt that includes a shaft having a distal end and a proximal end, wherein the distal end supports a pivotal attachment, and a toggle wing pivotably attached to the pivotal attachment. The assembly also includes a rigid stabilizing rod, the stabilizing rod having two ends and defining a first orifice and a second orifice, such that the axis of the second orifice is perpendicular to the axis of the first orifice and the second orifice is surrounded by an externally threaded annular lip, a cable having a first end and a second end, the first end attached to the proximal end of the toggle bolt and extending through second orifice, and a tube enclosing at least part of the length of the cable and having a first end threadably attached to the externally threaded annular lip, such that one end of the toggle bolt is extended through the distal end of the hollow screw.

The invention also broadly comprises a method of gradually laterally aligning a spine having a lateral curve using a spinal alignment assembly the spinal alignment assembly including a hollow bone screw having internal threads and an open proximal end and an open distal end, a second screw threadably inserted into the hollow bone screw; a toggle bolt that includes a shaft having a distal end, a middle section, and a proximal end, wherein the distal end supports a pivotal attachment, and a toggle wing pivotably attached to the pivotal attachment. The assembly also includes a rigid stabilizing rod, the stabilizing rod having two ends and defining a first orifice and a second orifice, wherein the axis of the second orifice is perpendicular to the axis of the first orifice and the second orifice is surrounded by an externally threaded annular lip, a cable having a first end and a second end, the first end attached to the proximal end of the toggle bolt and extending the second orifice, and a tube enclosing at least part of the length of the cable and having a first end threadably attached to the externally threaded annular lip and a second set screw threadably inserted into the tube, such that one end of the toggle bolt is extended through the distal end of the hollow screw. The gradual alignment method comprises the steps of screwing the hollow bone screw into a body of a vertebra of the spine; removing the second inner screw from the hollow bone screw; extending the toggle bolt through the hollow bone screw; placing the stabilizing rod on the hollow bone screw between the spine and the receiver; deploying the toggle wing on a convex side of the lateral curve; aligning the stabilizing rod laterally and longitudinally along the concave side of the lateral curve of the spine; enclosing at least part of the length of the cable in the tube such that the second end of the cable extends out of the back of a user; threadably attaching the tube to the receiver; attaching a cable tightening device at or near the second end of the cable; pulling the cable so as to pull the toggle bolt and the vertebra toward the concave side of the lateral curve; and tightening the second set screw to the cable to hold the pulled toggle bolt in the pulled position.

One object of the invention is to provide a device for aligning a lateral curve in a spine using a minimum amount of vertebral drilling sites;

A second object of the invention is to a spinal alignment assembly that can be used on either side of the spinal column.

A third object of the invention is to provide a device and method of spinal alignment in which corrective alignment is achieved gradually to avoid potential neurological and muscular damage. By gradually is meant over a period of several weeks to several months depending on the severity of the lateral curve.

BRIEF DESCRIPTION OF THE SEVERAL VIEWS OF THE DRAWINGS

The nature and mode of the operation of the present invention will now be more fully described in the following detailed description of the invention taken with the accompanying drawing Figures, in which:

FIG. 5A is a top view of stabilizing rod of the assembly of the present invention;

FIG. 5B is a side view of the stabilizing rod showing the receiver formed into the peak that defines a screw hole;

FIG. 5C is a cross section view taken along line 5C-5C in FIG. 5B;

FIG. 12 is a posterior view showing spinal column after the final pulling procedure; and, FIG. 12A is a cross section view similar to FIG. 5C showing the set screw holding the cable in place to maintain tension of the assembly after the final pulling procedure.

DETAILED DESCRIPTION OF EMBODIMENTS OF THE INVENTION

At the outset, it should be appreciated that like drawing numbers on different drawing views identify identical structural elements of the invention. It also should be appreciated that figure proportions and angles are not always to scale in order to clearly portray the attributes of the present invention.

While the present invention is described with respect to what is presently considered to be the preferred embodiments, it is understood that the invention is not limited to the disclosed embodiments. The present invention is intended to cover various modifications and equivalent arrangements included within the spirit and scope of the appended claims.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

Figure 1:
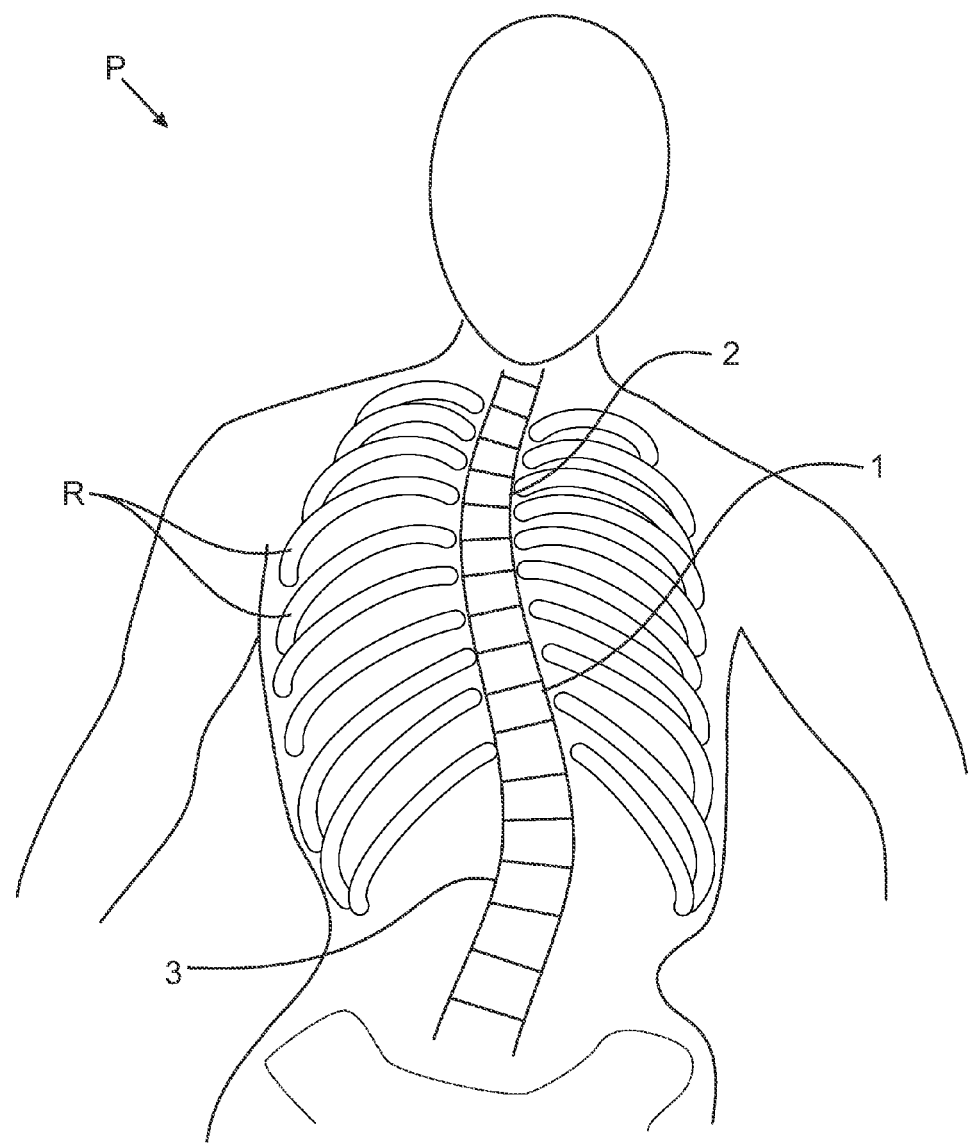
FIG. 1 is a stylized drawing of person with a spine afflicted with scoliosis.
Figure 2:
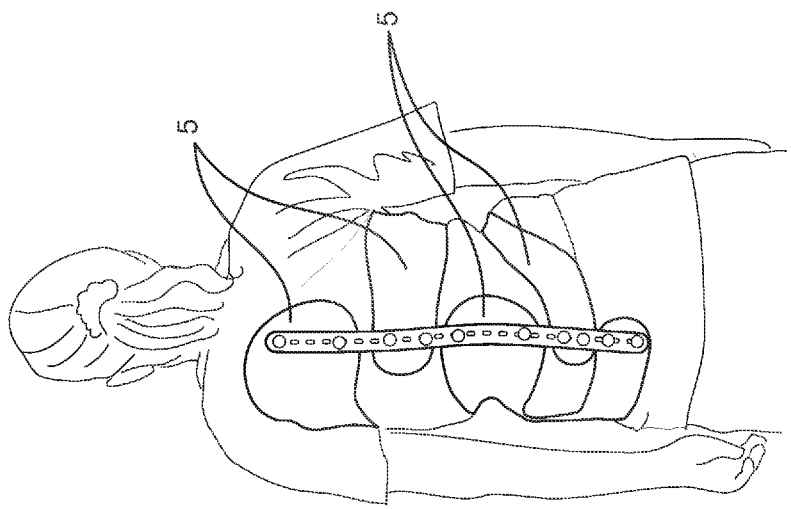
FIG. 2 is a rear view of a full body brace used by scoliosis patients.
Figure 2A:
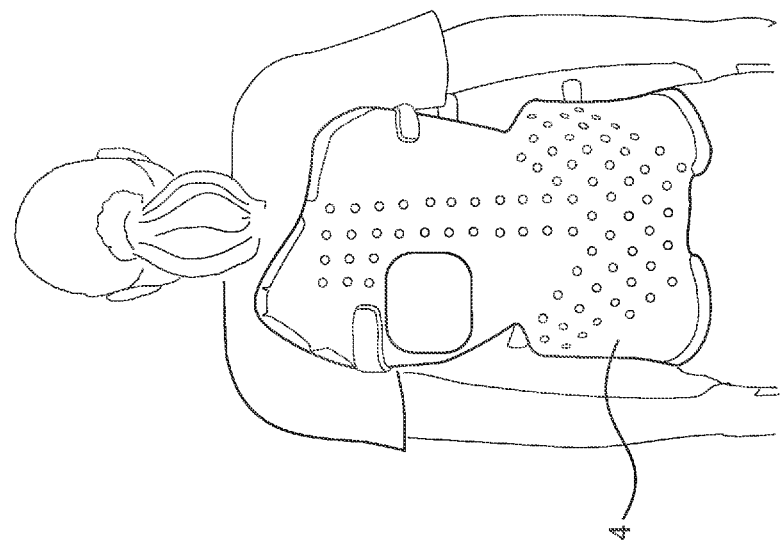
FIG. 2a is a rear view of a lighter brace used by scoliosis patients.

Adverting to the drawings, FIG. 1 is a stylized view of a person P with a spine afflicted with scoliosis. Spinal column 1 is shown to have two lateral curves—upper curve 2 and lower curve 3. Often the presence of one lateral curve will generate the formation of a second curve to compensate for the reduced spinal support of the body caused by one lateral curve. FIGS. 2 and 2A depict two different types of braces 4 and 5, respectively, used to prevent further deterioration of spinal alignment. In some cases, braces such as braces 4 and 5 may improve the condition, but they rarely enable the wearer to achieve a full recovery to a correct spinal alignment.

Figure 3:
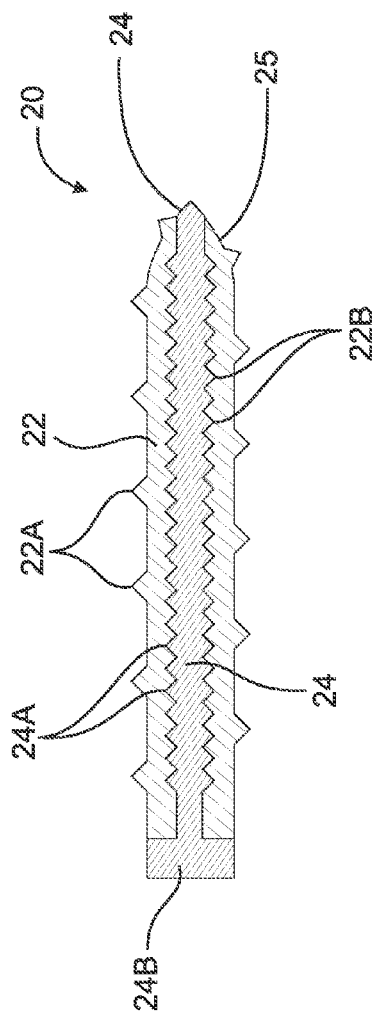
FIG. 3 is a cross section of a hollow bone screw having an outer shell and an inner screw threadably inserted therein.
Figure 4A:
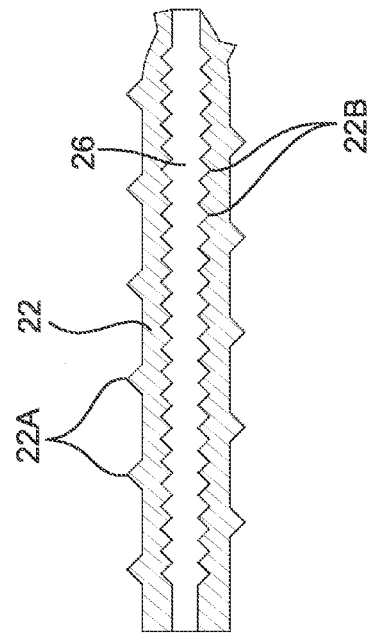
FIG. 4A depicts the outer shell with the inner screw removed leaving a lumen as a hollow space along the length of the outer shell.
Figure 4:
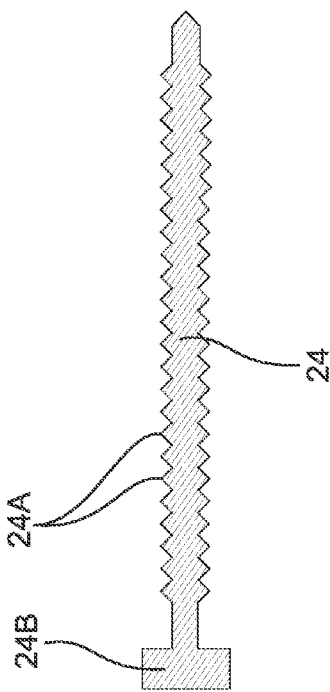
FIG. 4 demonstrates the inner screw as separated from the outer shell.

FIG. 3 is a cross section of hollow bone screw 20. Outer screw shell 22 is externally threaded with threads 22a to enable it to be screwed into the body of a vertebra as described below. Inner screw 24 is also externally threaded with threads 24a to threadably connect with internal threads 22b of outer screw shell 22. Preferably cap 24b is attached to the proximal end of inner screw 24. FIGS. 4 and 4A demonstrate how inner screw 24 can be separated from outer shell 22 leaving lumen 26 as a hollow space along the length of outer shell 22.

FIG. 5A is a top view of stabilizing rod 30 ("rod 30"). Preferably the ends 30a of rod 30 are curved to provide the advantage of being able to move more easily along the spine and longitudinal muscles along the spine. Receiver complex 32 ("receiver 32") extends from the surface of rod 30 to form a peak which defines screw hole 34. FIG. 5B is a side view of rod 30 showing receiver 32 formed into the peak that defines screw hole 34 (not seen in FIG. 5B). Also seen is aperture 36, defined by part of one side of receiver 32, and set screw 37 set into the same side of receiver 32.

FIG. 5C is a cross section view taken along line 5C-5C in FIG. 5B. Set screw 37 is shown set into receiver 32. It can be seen that aperture 36 and set screw 37 have parallel longitudinal-axes and both of these axes are substantially perpendicular to the axis 34a of screw hole 34. Annular lip 38 surrounds aperture 36 and set screw 37 and is externally threaded.

Figure 6:
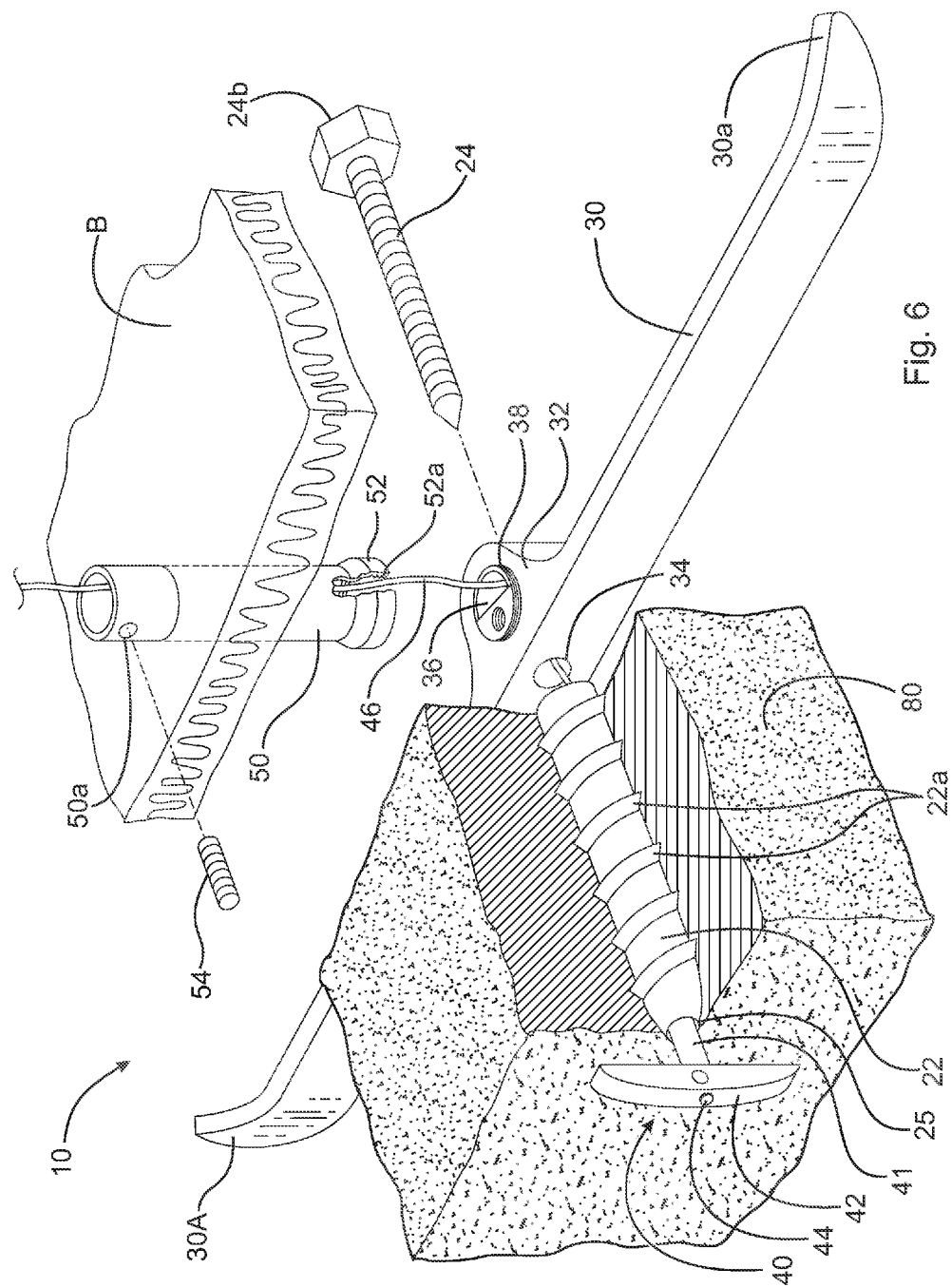
FIG. 6 is side perspective exploded view of the assembly of the present invention attached to a vertebra in the spinal column of the spine to be aligned.

FIG. 6 is side perspective exploded view of assembly 10 attached to a vertebra 80 in the spinal column of the spine to be aligned. Initially, hollow screw 20 is extended into screw hole 34 and is screwed into body 80 of the target vertebra until the distal end point 25 emerges slightly from the distal side, which preferably is at or near the peak of the convex curve of the laterally curved spinal column 1. Inner screw 24 is then removed from outer shell 22 thereby opening lumen 26. Toggle bolt 40 having shaft 41 with a distal end and a proximal end (not seen in FIG. 6) and deployable wings 42 is guided through lumen 26 from the proximal side of vertebra 80 until it extends past distal end point 25 at the distal end of hollow screw 20. Preferably, toggle bolt 40 includes pivot attachment 44 to which wings 42 are attached. Wings 42 are deployed (opened out) as shown in FIG. 6 and pulled against the convex side of vertebra 80. Cable 46, attached to the proximal end of shaft 41, extends out the proximal end of lumen 26 and guided into screw hole 34 and up aperture 36. This perpendicular turn is preferably guided by curved wall 36b of aperture 36. Persons of skill in the art will recognize that cable 46 may be threaded from distal end point 25 toward the proximal end of lumen 26 with wings 42 deployed at distal end point 25. In addition, equivalent devices having expanded or expandable components positioned similarly to wings 42 may be used in place of toggle bolt 40 as long as they provide satisfactory support for pulling cable 46 as described below.

Cable 46 is guided through tube 50 which extends posteriorly through back B. Lip 52 at one end of tube 50 included internal threads 52a to enable tube 50 to be threadably attached to annular lip 38. Set screw 54 is screwed into threaded tube aperture 50a to hold cable 46 in place.

Figure 7:
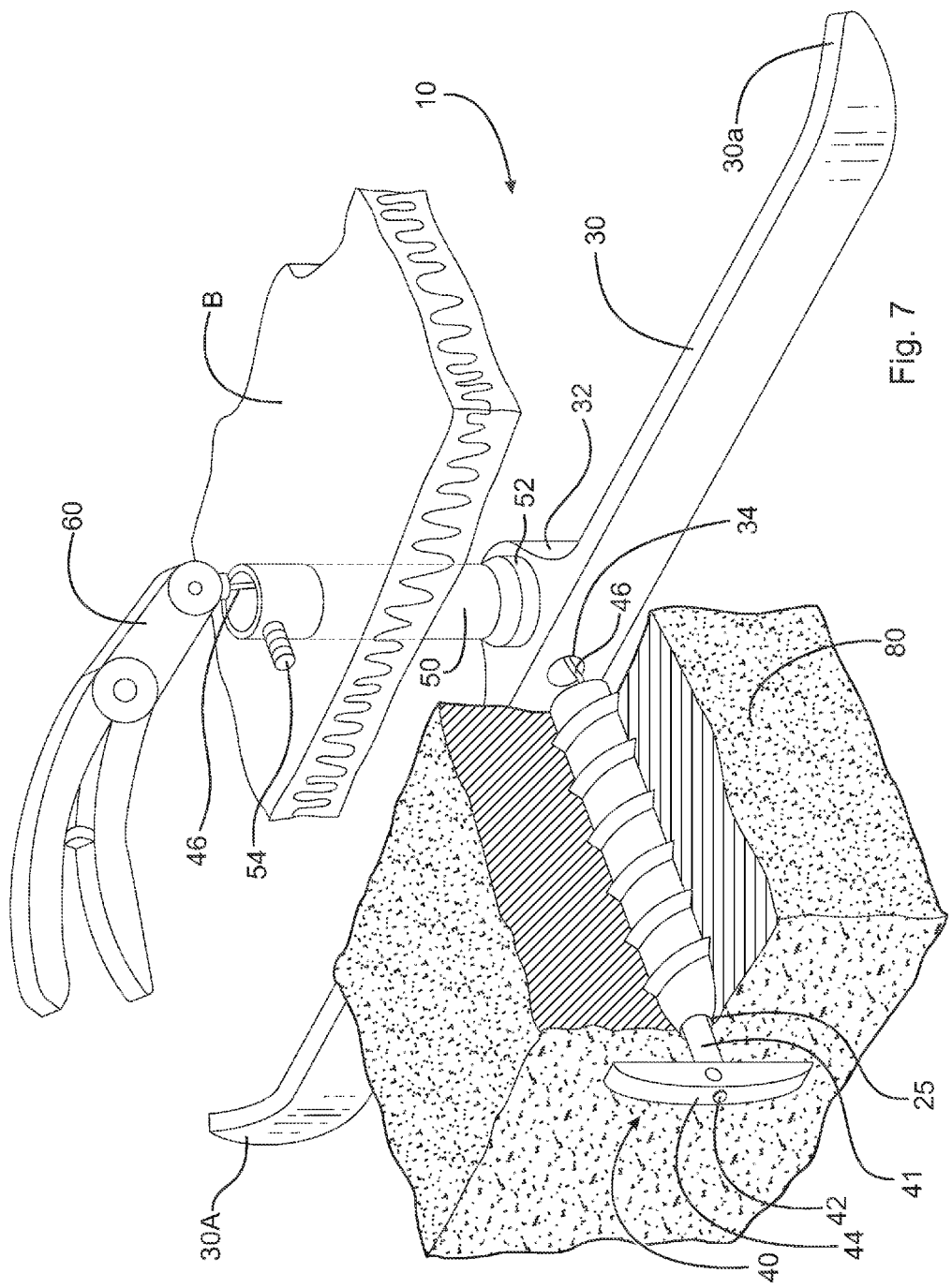
FIG. 7 is a side perspective view of the assembly showing a pulling tool attached to the end of the pulling cable.

FIG. 7 is a side perspective view of assembly 10 showing pulling tool 60 attached to the end of cable 46. Cable 46 has sufficient length to extend from the proximal end of the toggle bolt shaft to outside the back to be attached to pulling tool 60. Examples of pulling tools are winch or reel-type devices, come-along, pliers, or other suitable devices that are able to repeatedly apply a pulling force to cable 46 which pulls the convex apex of laterally curved spinal column 1 at the point where toggle wing 42 contacts vertebral body 80. Tube 50 is threadably attached to annular lip 38. It will be understood that other vertebra are positioned above and below target vertebra 80. Because rod 30 is placed along the concave curve of the spine, it is possible that it will not contact vertebra 80 during some or all of the alignment process as is shown in FIG. 7. The perpendicular turn allows the force vectors on cable 46 to be directed out of back B so that the lungs and surrounding viscera can be avoided.

Figure 8:
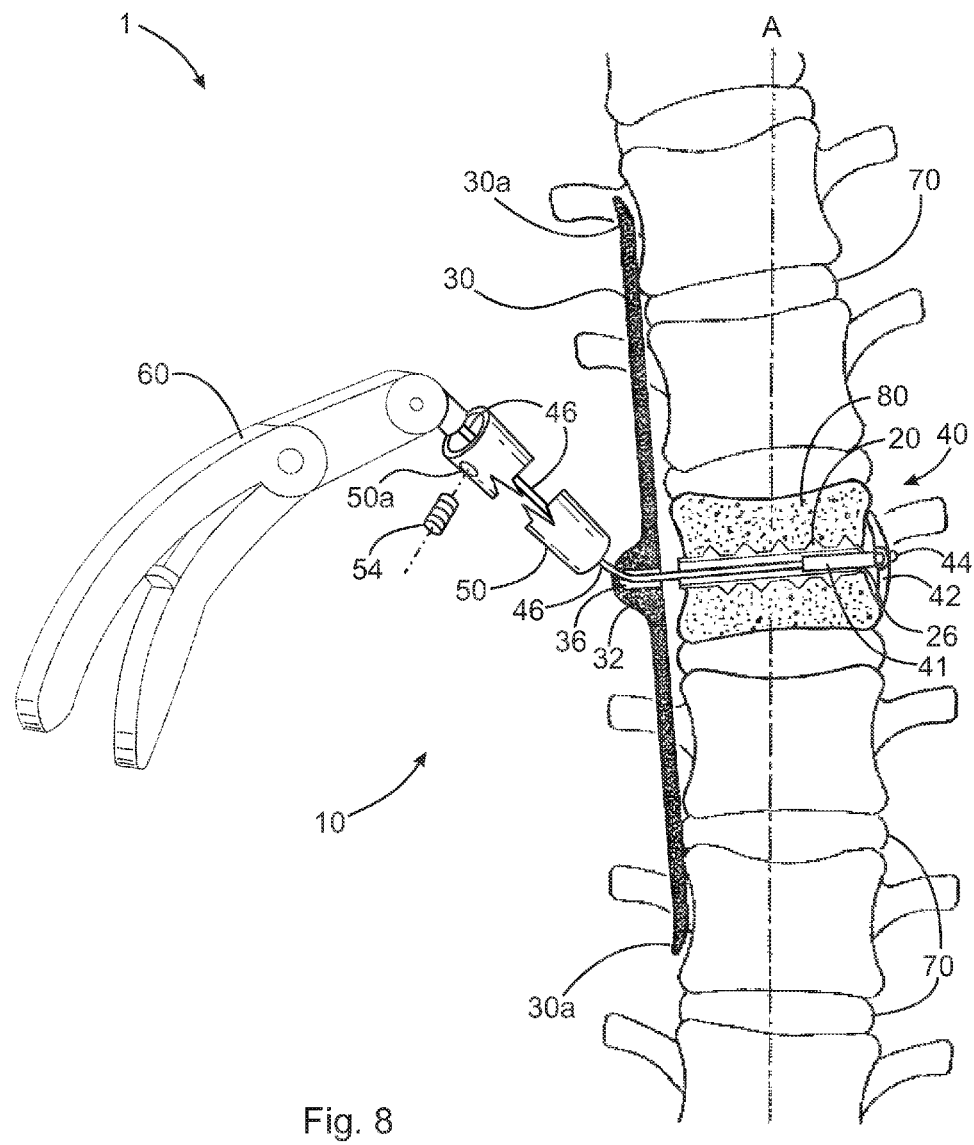
FIG. 8 is a top or posterior view of a laterally curved spinal column with the alignment assembly in place.

FIG. 8 is a top or posterior view of laterally curved spinal column 1 with alignment assembly 10 in place as shown in FIG. 7. Axis A represents what the longitudinal axis of spinal column 1 would be when straightened to the ideal anatomical position. Toggle bolt 40 is depicted with deployed wings 42 contacting vertebra 80. Vertebral discs 70 are shown alternately placed within spinal column 1 between each vertebra. The attachment of tube 50 to annular lip 38 is depicted in cut out form to show cable 46 extending from toggle bolt 40 through lumen 26 and aperture 36 into tube 50. In a preferred practice, tube 50 would be attached to annular lip 38. The further or distal end of cable 46 is attached to pulling tool 60. Rod 30 is placed laterally and longitudinally along spinal column 1. It can be seen that because rod 30 is preferably on the concave side of the lateral spinal curve, it may not contact curved spinal column 1 where cable 46 emerges from spinal column 1 on the concave or proximal side.

Figure 9:
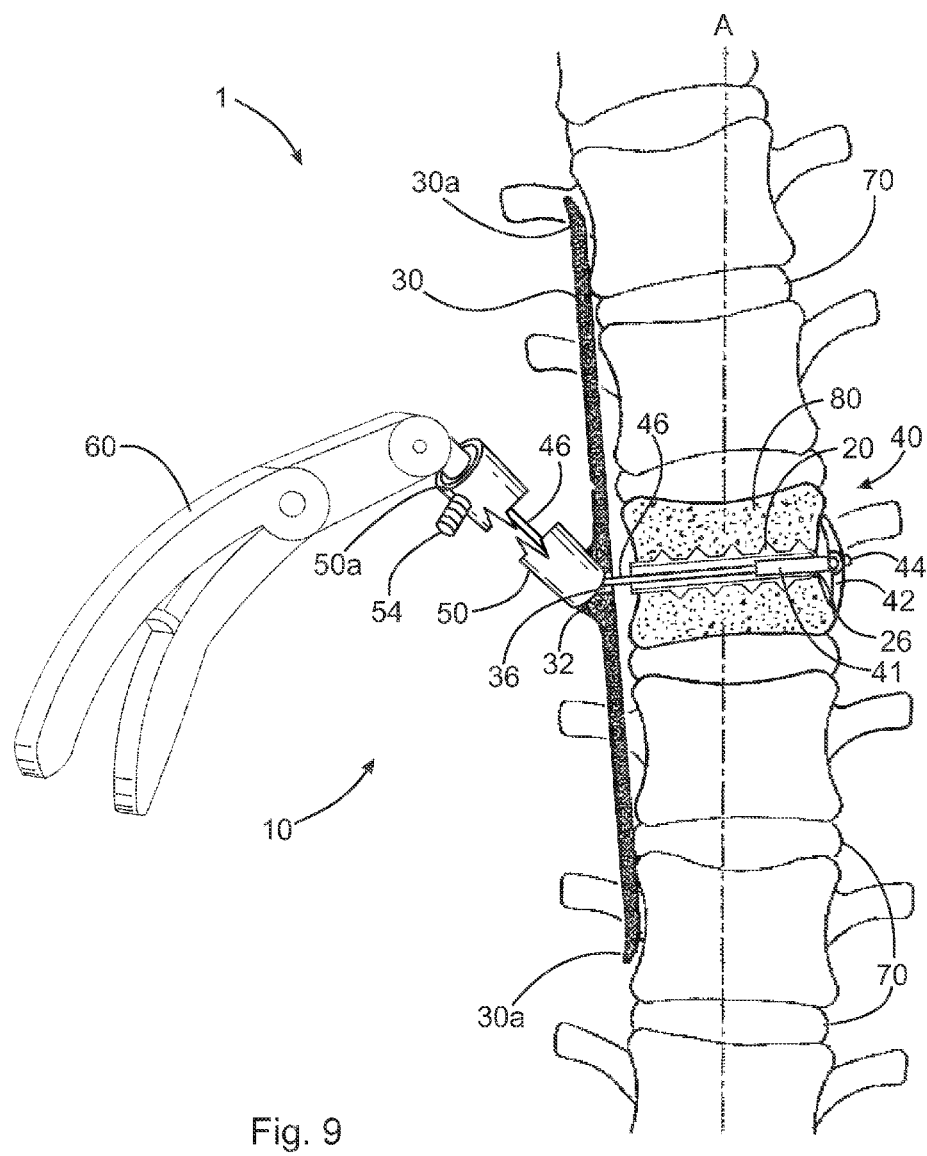
FIG. 9 a top or posterior view showing the assembly holding the spinal column in place after a pulling procedure.

During the pulling procedure, set screw 54 is loosened or removed from tube aperture 50a. Pulling tool 60 applies pulling force across spinal column 1 onto wings 42. This pulls spinal column 1 against stabilizing rod 30 forcing wings 42 and consequently vertebra 80 toward rod 30 thereby reducing the lateral curve. After sufficient movement, tube set screw 54 is threaded into tube aperture 50a to hold the pulled cable and spinal column in the new straighter position. After a period of time to allow muscles and nerves and spinal column 1 to adjust to the new position, the pulling procedure is repeated with spinal column 1 again being pulled against rod 30 to an even straighter position relative to axis A. FIG. 9 shows assembly 10 after a pulling procedure with tube 50 attached to rod 30 at annular lip 38 (not shown in FIG. 9). By following the sequence of pulling, tightening, and waiting, spinal column 1 is gradually brought closer to proper alignment. By gradual or gradually is meant that alignment may be achieved of a period of as little as one or two days to as long as 6 months, although in mild cases of scoliosis 5-15 minutes to one day may be possible. Normally, an alignment period may range from a week to about three months, but persons of skill in the art will recognize that the length of the alignment period will depend on such factors as the severity of the lateral curve, the age of the patient, and the strength of the surrounding neuromuscular structure as well as other factors.

Figure 10:
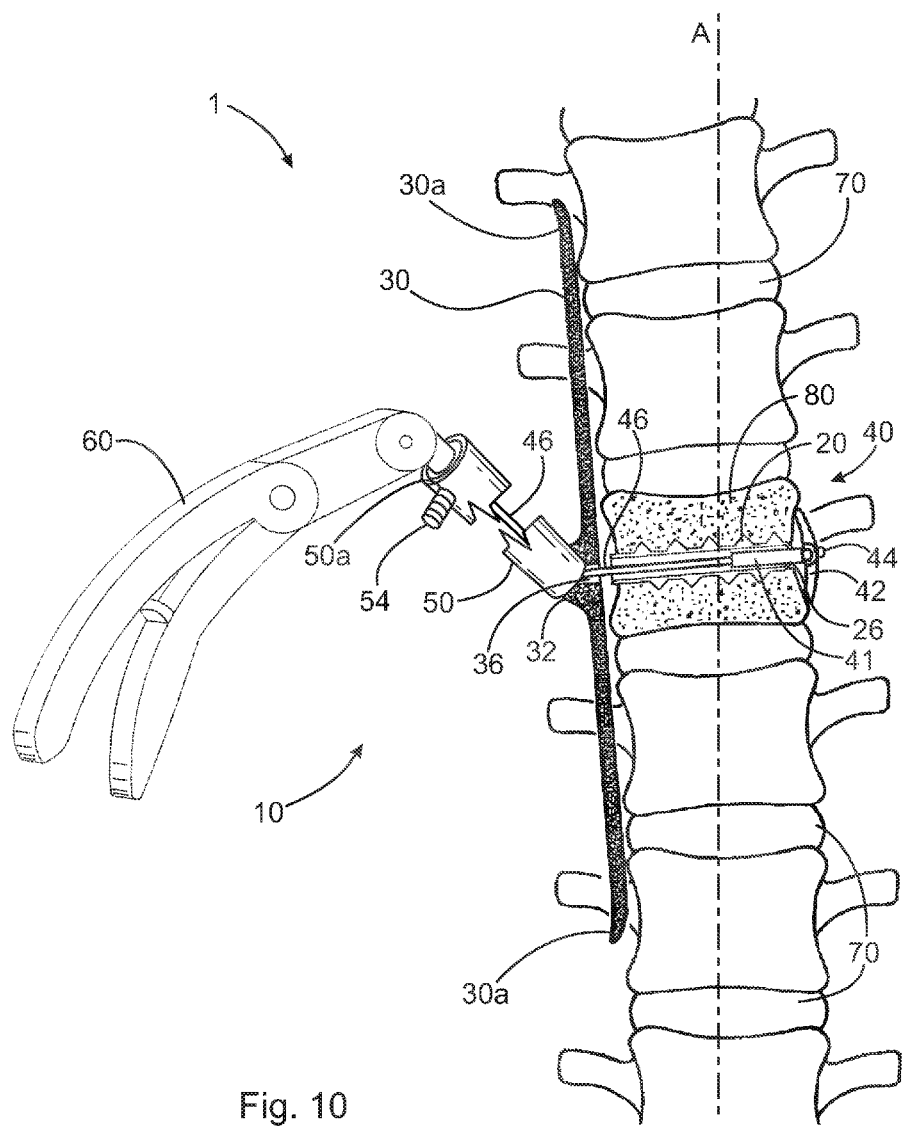
FIG. 10 shows spinal column moved to a straighter position relative to the axis after a succeeding pulling procedure.
Figure 10A:
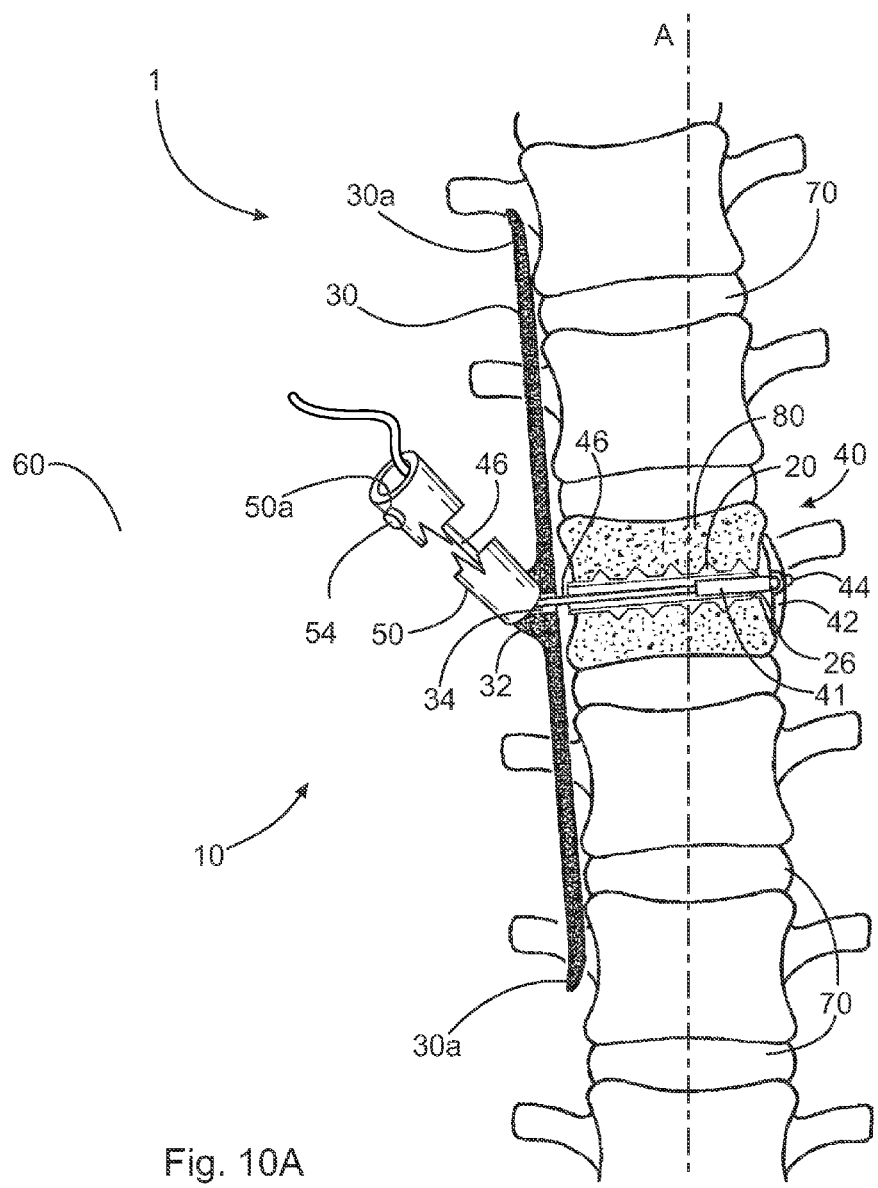
FIG. 10A shows the assembly with the pulling tool removed and the tube set screw screwed into the tube aperture to hold the cable in place between pulling procedures.

FIG. 10 shows spinal column 1 moved to a straighter position relative to axis A after a succeeding pulling procedure. Rod 30 is shown closer to spinal column 1 as spinal column 1 is pulled straighter. It can also be seen that curved ends 30*a* provide an advantage over straight ends in that it allows stabilizing rod 30 to move along spinal column 1 with less if any interference with elements of spinal column 1. FIG. 10A shows assembly 10 with pulling tool removed and tube set screw 54 screwed into tube aperture 50*a* holding cable 46 in place between pulling procedures.

Figure 11:
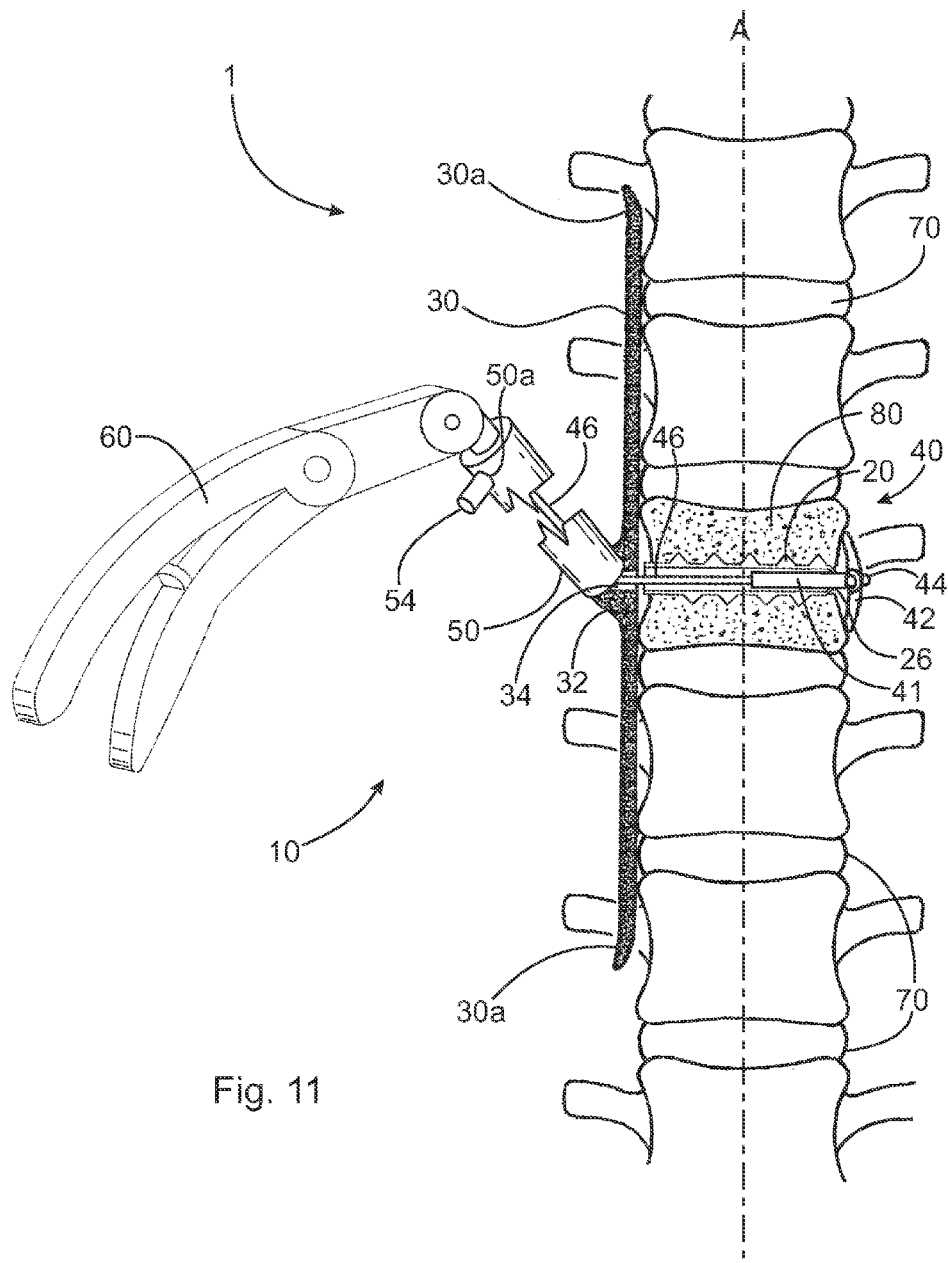
FIG. 11 is the same posterior view showing the results of the final pulling procedure in which the lateral curve of the spinal column is significantly reduced if not eliminated.

FIG. 11 is the same posterior view showing the results of the final pulling procedure in which the lateral curve of spinal column 1 is significantly reduced if not eliminated. It can be seen that the middle section of stabilizing rod 30 is pulled close to vertebra 80 at the insertion point of hollow bone screw 20.

FIG. 12 is a posterior view showing spinal column 1 after the final pulling procedure. Tube 50 is removed through the back of the patient. Stabilizing rod 30 is left in place holding spinal column 1 in place against toggle bolt wings 42 with the holding force transmitted on cable 46 in lumen 26.

FIG. 12A is a cross section view similar to FIG. 5C in which set screw 37 is shown screwed down into screw hole 34 to hold (fix) cable 46 in place under tension after the final pulling procedure. Set screw 37 is screwed in place before set screw 54 is loosened to constantly maintain tension in cable 46 to enable assembly 10 to hold spinal column 1 in the final position. Set screw 37 may be tightened using appropriate conventional or arthroscopic instruments known to those skilled in the art. Thus, cable 46 is held in place under tension by its attachment to toggle bolt 40 at the distal end and by set screw 37 at the proximal end. After set screw 37 holds cable 46, the remaining "tail" of cable 46 extending past set screw 37 can be cut close to or inside aperture 36. In one embodiment, a cap may be placed over annular lip 38.

Thus it is seen that the objects of the invention are efficiently obtained, although changes and modifications to the invention should be readily apparent to those having ordinary skill in the art, which changes would not depart from the spirit and scope of the invention as claimed.

I claim:

1. An assembly for performing a gradual lateral spinal alignment of a spine, said spine to be aligned having a lateral curve, said lateral curve having a convex side and an opposite concave side, comprising:
    a hollow bone screw having internal threads and an open proximal end and an open distal end;
    a second screw threadably insertable into said hollow bone screw;
    a toggle bolt including:
        a shaft having a distal end and a proximal end, wherein said distal end supports a pivotal attachment; and,
        at least one toggle wing pivotably attached to said pivotal attachment;
    a rigid stabilizing rod, said stabilizing rod having two ends and a receiver complex, said receiver complex defining a screw hole and an aperture, wherein the axis of said aperture is substantially perpendicular to the axis of said screw hole and said aperture is surrounded by an externally threaded annular lip;
    a cable having a first end and a second end, said first end attached to said proximal end of said toggle bolt shaft and extending through said aperture; and,
    a tube enclosing at least part of the length of said cable and having a first end threadably attached to said externally threaded annular lip;
    wherein one end of said toggle bolt is extended through said distal end of said hollow screw.

2. The assembly for performing a gradual lateral spinal alignment as recited in claim 1 wherein said stabilizing rod further comprises an internally threaded bore hole, said internally threaded bore hole having an axis substantially parallel to the axis of said aperture and arranged to receive a first set screw.

3. The assembly for performing a gradual lateral spinal alignment as recited in claim 1 wherein said distal end of said hollow bone screw is configured to extend transversely through the body of a vertebra of said spine, said distal end is configured to extend to at least the convex side of said lateral curve.

4. The assembly for performing a gradual lateral spinal alignment as recited in claim 1 wherein said stabilizing rod is configured to lay laterally and longitudinally along said spine.

5. The assembly for performing a gradual lateral spinal alignment as recited in claim 4 wherein said stabilizing rod is configured to extend longitudinally along said spine on the concave side of said spine.

6. The assembly for performing a gradual lateral spinal realignment as recited in claim 1 wherein said two ends of said rigid stabilizing rod are curved.

7. The assembly for performing a gradual lateral spinal alignment as recited in claim 1 wherein said tube further comprises a second internally threaded tube aperture arranged to receive a second set screw.

8. The assembly for performing a gradual lateral spinal alignment as recited in claim 1 further comprising a cable pulling tool releasably attached at or near said second end of said cable.

9. The assembly for performing a gradual lateral spinal realignment as recited in claim 1 wherein said cable comprises sufficient length to extend from said proximal end of said toggle bolt to outside the back of a user.

10. A method of gradually laterally aligning a spine having a lateral curve using a spinal alignment assembly said spinal alignment assembly including:
    a hollow bone screw having internal threads and an open proximal end and an open distal end;
    a second screw threadably insertable into said hollow bone screw;
    a toggle bolt including:
        a shaft having a distal end and a proximal end, wherein said distal end supports a pivotal attachment; and,
        at least one toggle wing pivotably attached to said pivotal attachment;
    a rigid stabilizing rod, said stabilizing rod having two ends and a receiver complex, said receiver complex defining a screw hole and an aperture, wherein the axis of said aperture is substantially perpendicular to the axis of said screw hole and said aperture is surrounded by an externally threaded annular lip;
    a cable having a first end and a second end, said first end attached to said proximal end of said toggle bolt shaft and extending through said aperture; and,
    a tube enclosing at least part of the length of said cable and having a first end threadably attached to said externally threaded annular lip;
    wherein one end of said toggle bolt is extended through said distal end of said hollow screw, said method comprising:
    extending said hollow bone screw into said screw hole;
    screwing said hollow bone screw into a body of a vertebra of said spine;
    removing said second screw from said hollow bone screw;
    guiding said toggle bolt through said hollow bone screw;
    deploying said toggle wing on a lateral side of said lateral curve;

aligning said stabilizing rod laterally and longitudinally along the lateral curve of said spine;

enclosing at least part of the length of said cable in said tube such that said second end of said cable extends out of the back of a user;

threadably attaching said tube to said receiver complex;

attaching a cable tightening device at or near said second end of said cable;

pulling said cable so as to pull said toggle bolt and said vertebra toward said concave side of said lateral curve; and tightening a first set screw to said cable to hold said pulled toggle bolt in said pulled position.

11. The method of gradually laterally aligning a spine having a lateral curve as recited in claim 10 further comprising loosening said first set screw and repeating said pulling and said tightening steps.

12. The method of gradually laterally aligning a spine having a lateral curve as recited in claim 10 further comprising fixing the cable proximate said receiver.

13. The method of gradually laterally aligning a spine having a lateral curve as recited in claim 12 wherein said fixing device is a second set screw.

14. The method of gradually laterally aligning a spine having a lateral curve as recited in claim 10 further comprising removing said tube and cutting said cable near said second set screw.

15. The method of gradually laterally aligning a spine having a lateral curve as recited in claim 10 wherein said stabilizing rod lies laterally and longitudinally along said spine on said concave side of said lateral curve, said deployed toggle wing contacting said vertebra on said convex side.

16. The method of gradually laterally aligning a spine having a lateral curve as recited in claim 10 wherein said cable tightening device is a winch.

17. The method of gradually laterally aligning a spine having a lateral curve as recited in claim 10 wherein said cable tightening device is a come-along.

18. The method of gradually laterally aligning a spine having a lateral curve as recited in claim 10 wherein said cable tightening device is a pliers.

* * * * *